United States Patent [19]
Taylor et al.

[11] Patent Number: 5,919,133
[45] Date of Patent: *Jul. 6, 1999

[54] CONFORMAL WRAP FOR PULSE OXIMETER SENSOR

[75] Inventors: James H. Taylor, Broomfield, Colo.; Michael Petterson, Dana Point, Calif.

[73] Assignee: Ohmeda Inc., Liberty Corner, N.J.

[21] Appl. No.: 08/826,695

[22] Filed: Apr. 7, 1997

Related U.S. Application Data

[60] Provisional application No. 60/016,356, Apr. 26, 1996.
[51] Int. Cl.⁶ .................................................. A61B 5/00
[52] U.S. Cl. .................................. 600/323; 600/344
[58] Field of Search .................................. 600/310, 322, 600/323, 340, 344, 476, 479

[56] References Cited

U.S. PATENT DOCUMENTS

| | | | |
|---|---|---|---|
| 4,825,879 | 5/1989 | Tan et al. | 600/344 |
| 4,876,587 | 10/1989 | Hilton et al. | 357/70 |
| 5,170,786 | 12/1992 | Thomas et al. | 128/633 |

FOREIGN PATENT DOCUMENTS

| | | |
|---|---|---|
| 0 104 772 A2 | 4/1984 | European Pat. Off. . |
| 0 127 947 A2 | 12/1984 | European Pat. Off. . |
| 0 538 631 A1 | 4/1993 | European Pat. Off. . |
| 3809084 A1 | 9/1989 | Germany . |
| WO 92/21280 | 12/1992 | WIPO . |
| WO 94/12096 | 6/1994 | WIPO . |

*Primary Examiner*—Lee Cohen
*Assistant Examiner*—Eric F. Winakur
*Attorney, Agent, or Firm*—Holme Roberts & Owen

[57] ABSTRACT

The present invention is directed to a pulse oximeter sensor and an attached flexible carrier for measuring the oxygen saturation of a patient's blood. The carrier includes a compressible material, such as foam, for contacting the patient's skin and the sensor that applies a substantially uniform pressure to the skin.

39 Claims, 12 Drawing Sheets

CONFORMAL WRAP FOR PULSE OXIMETER SENSOR

The present application claims priority from copending U.S. Provisional Application Ser. No. 60/016,356 entitled "CONFORMAL WRAP FOR OXIMETER SENSOR", filed Apr. 26, 1996, which is incorporated herein by reference in its entirety.

FIELD OF THE INVENTION

The present invention is generally directed to photoplethysmographic measurement instruments and specifically to pulse oximeter sensors for premature infants.

BACKGROUND OF THE INVENTION

Infants born prematurely (known as "premature infants") are often extremely fragile and require specialized medical care. An important concern of such medical care is the condition of the infant's respiratory system, which is one of the last organs to fully develop in an infant before birth. Deprivation of oxygen caused by a premature infant's underdeveloped respiratory system can have serious consequences.

Instruments, such as pulse oximeters, are commonly used to identify problems with a patient's respiratory system. The color of the blood (i.e., the amounts of red and infrared radiation absorbed by the blood) is a function of the oxygen saturation of the heme in the blood's hemoglobin. For example, heme that is saturated with oxygen appears bright red because saturated heme is highly permeable to red light. In contrast, heme that is deoxygenated appears dark and bluish as it is less permeable to red light. A pulse oximeter measures the oxygen saturation of arterial blood by irradiating the blood with red and infrared radiation generated by one or more emitters, receiving the unabsorbed radiation with a detector, and, based on the unabsorbed radiation component, determining the corresponding amounts of the red and infrared radiation that are absorbed by the heme in the blood.

There are a number of competing design considerations for pulse oximeters, particularly when the oximeters are to be applied to premature infants. First, the pulse oximeters should have the ability to achieve a reliable interface between the emitter and detector in the sensor and the patient's skin. This is particularly a challenge when the oximeter is applied to premature infants due to the small size of the infants at birth. Second, the pulse oximeter should be adapted for ready application and removal from the patient with a minimal amount of pair or discomfort for the patient. Finally, the pulse oximeter should provide, particularly in the case of premature infants, a gentle interface with the patient's skin. As will be appreciated, the gelatinous skin and other tissue of premature infants is typically not fully developed and therefore can be extremely fragile.

SUMMARY OF THE INVENTION

It is an objective of the present invention to provide a photoplethysmographic oximeter and, more particularly, a pulse oximeter sensor that provides a gentle interface with sensitive tissue such as that of premature infants.

Another objective of the present invention is to provide a pulse oximeter sensor having a reliable interface between the emitter and detector of the pulse oximeter sensor and the patient's skin. A related objective is to provide a pulse oximeter sensor providing such an interface for premature infants.

A further objective of the present invention is to provide a pulse oximeter sensor adapted for ready application and removal with a minimum of discomfort and damage to the patient.

These and other objectives are addressed by the pulse oximeter sensor of the present invention. The pulse oximeter system includes a pulse oximeter processing and display unit, a pulse oximeter sensor, and a flexible carrier for the sensor. The pulse oximeter sensor (or measuring means for measuring the oxygen content of a patient's blood) is an assembly of one or more emitter(s) for providing a spectral content, a detector for measuring the unabsorbed radiation component(s), electronic circuitry connecting the detector and emitter to the pulse oximeter processing and display unit, and the housing enclosing these components.

The flexible carrier (or flexible carrier means for engaging the measuring means with the patient's tissue) includes a compressible material, a backing material, and a fastener, which collectively provide a non-adhesive contact between the device and the patient's skin. In particular, the fastener permits a first portion of the carrier to selectively and releasably engage a second portion. At least one of the first and second portions can have a longitudinal length to permit the carrier to be adjustably engaged with body parts having a wide variety of sizes.

The pulse oximeter sensor is nested in a recess of the flexible carrier. In this position, the pulse oximeter sensor is substantially surrounded by compressible material, such as foam. When the pulse oximeter sensor and carrier are applied to the patient's skin (or other tissue), the surfaces of the pulse oximeter sensor and the surrounding compressible material contacting the patient's skin are substantially conformal with the skin.

The sensor and flexible carrier can provide a reliable interface between the emitter(s) and detector on the one hand and the patient's skin on the other, even for extremely small patients such as premature infants. The sensor and carrier can be readily applied and removed from the patient's skin with a minimum amount of discomfort or damage. This is due in part to the gentle interface between the faces of the sensor and carrier on the one hand and the patient's skin on the other. The flexible carrier can substantially immobilize the emitter(s) and detector relative to the patient's skin to provide an accurate measurement of the oxygen saturation of the patient's blood.

The sensor is nested in the recess in the compressible material prior to use such that, when the sensor is engaged with the patient's skin, there are virtually no pressure points (i.e., points of elevated pressures relative to surrounding areas) on the sensor. When the carrier is attached to or looped around a body part, the compressible material conforms substantially to the contours of the body part and therefore applies a substantially even pressure to the patient's skin. This is made possible in one embodiment by the front surface of the sensor and the front surface of the surrounding compressible material providing a substantially continuous and level surface after application to the patient's skin. Such a surface inhibits tissue damage caused by abrasion, scratching, brusing, pressure necrosis, and/or impaired blood flow. It further enables the front surface of the sensor to contact the patient's skin without gaps disposed between the front surface and the patient's skin.

The sensor and carrier can be contacted with the patient's skin without using adhesive or suctional forces to further reduce the likelihood of patient pain or discomfort or tissue damage. Preferably, the carrier is looped about a body part and attaches only to itself. In a preferred embodiment of the present invention, the fastener includes a plurality of hooks that engage a plurality of matching loops to permit the carrier to be formed into a loop around the body part. This hook-and-loop arrangement permits the carrier to be readily separable from the patient's skin. Therefore, it significantly more comfortable for patients compared to sensors that are bonded directly to the patient's skin and is simple to use. The carrier can be easily and readily readjusted to engage a desired portion of a body part of a patient. The compressible material permits the carrier to be adjusted to a different location often without readjustment of the fastener.

The compressible material in the sensor can be foam, neoprene, rubber, fabric, and composites thereof. The compressible material has a plurality of void spaces to permit compression. Preferably, the volume occupied by the compressible material is at least about 50% by volume void space. The compressible material has a preferred thickness ranging from about 0.4 to about 1.5 cm.

The relative thicknesses of the sensor and the compressible material can vary depending upon the application. In one embodiment of the present invention, the front surface of the sensor and the front surface of the compressible material are at substantially the same level (e.g., the sensor and compressible material have substantially the same thicknesses) before the sensor and carrier are applied to the patient. In another embodiment, the front surface of the sensor is lower than the front surface of the compressible material (e.g., the sensor has a lesser thickness than the compressible material) before the sensor and carrier are applied to the patient. The compression of the compressible material upon application to the patient lowers the upper surface to substantially the same level as the front surface.

In one embodiment, the thickness of the sensor is about 90% or less of the thickness of the compressible material.

The present invention further includes a method for measuring the oxygen saturation of a patient's bloodstream using a pulse oximeter. The method includes the steps: (a) contacting the compressible material of the carrier and the sensor with the patient's skin; (b) engaging a portion of the carrier with another portion of the carrier to attach the carrier to the body part; (c) passing radiation from the emitter in the sensor through the bloodstream such that a portion of the radiation is absorbed by the bloodstream and a portion of the radiation is passed by the bloodstream; (d) receiving at least a portion of the passed radiation portion with the detector in the sensor; and (e) determining the oxygen saturation of the bloodstream based on the received passed portion radiation portion.

The sensor and carrier can be inexpensive and therefore disposed of after one or a few applications. In this regard, the sensor and carrier are preferably composed of relatively inexpensive materials and, due to their small number of component parts, are simple to manufacture. The sensor and carrier are thus preferable to existing sensing devices which are composed of relatively expensive materials, have a large number of component parts, and/or are expensive to manufacture.

DETAILED DESCRIPTION

Referring to FIGS. 1–6, a sensing device 20 according to the present invention includes a pulse oximeter sensor 24 for measuring the oxygen saturation of a patient's blood and a flexible carrier 28 for non-adhesively engaging the patient's skin in the vicinity of the blood oxygen saturation measurement. The sensor 24 includes an emitter assembly 32 for providing a spectral content, a detector 36 for detecting unabsorbed radiation, and electrical circuitry such as conductive lead 44 for communicating measurement information to a pulse oximeter processing and display unit (not shown), all contained within a substantially light impermeable housing 48. The flexible carrier 28 includes a backing material 52 for imparting strength to the flexible carrier, a compressible material 56 for providing a gentle interface for the patient's skin, and an attachment strap 60 for forming the carrier 28 into a loop for engaging a patient's body part, such as an infant's foot or hand. The sensing device 20 attaches to the body part without adhesive or suctional forces between the sensing device and the patient's skin.

The sensor 24 is recessed in a cavity 64 having substantially the same size and shape as the sensor 24 to permit the front surface 68 of the sensor to be substantially level with the front surface 72 of the compressible material 56. The sensor front surface 68 and front surface 72 of the compressible material are substantially level with few, if any (and preferably no), raised areas to provide a continuous surface contacting the patient's skin. That is, the height "$H_C$" of the front surface 72 above the front surface 76 of the backing material, which typically ranges from about 0.4 to about 1.5 cm, is no less than the height "$H_S$" of the sensor front surface 68 above the front surface 76 of the backing material. In this manner, the sensor front surface and front surface of the compressible material apply to the patient a uniform pressure substantially uniformly across the area of the two front surfaces and avoids pressure points (i.e., points of elevated pressures relative to surrounding areas). The cavity 64 is typically formed by removing a portion of the compressible material using a cutting die having the same size and shape as the sensor.

To adequately shield the perimeter edges 80 of the sensor from contacting the patient's skin and forming a pressure point, a substantial portion of the perimeter of the sensor is adjacent to compressible material. Preferably, at least about 75% and more preferably at least about 85% of the perimeter is adjacent to the compressible material.

Figure 1:
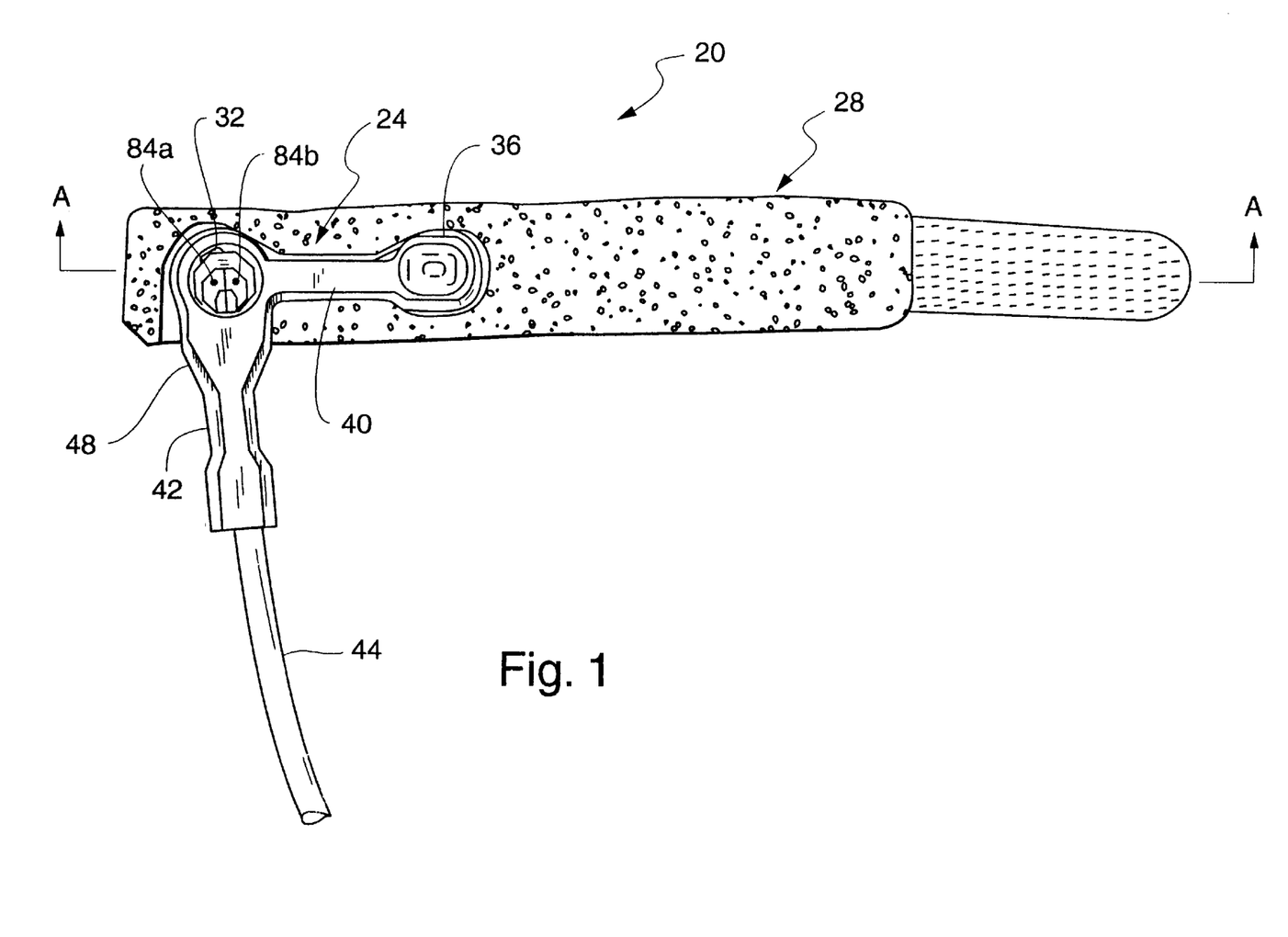
FIGS. 1 and 2 are plan views of the flexible carrier according to the present invention with and without the sensor, respectively.
Figure 2:
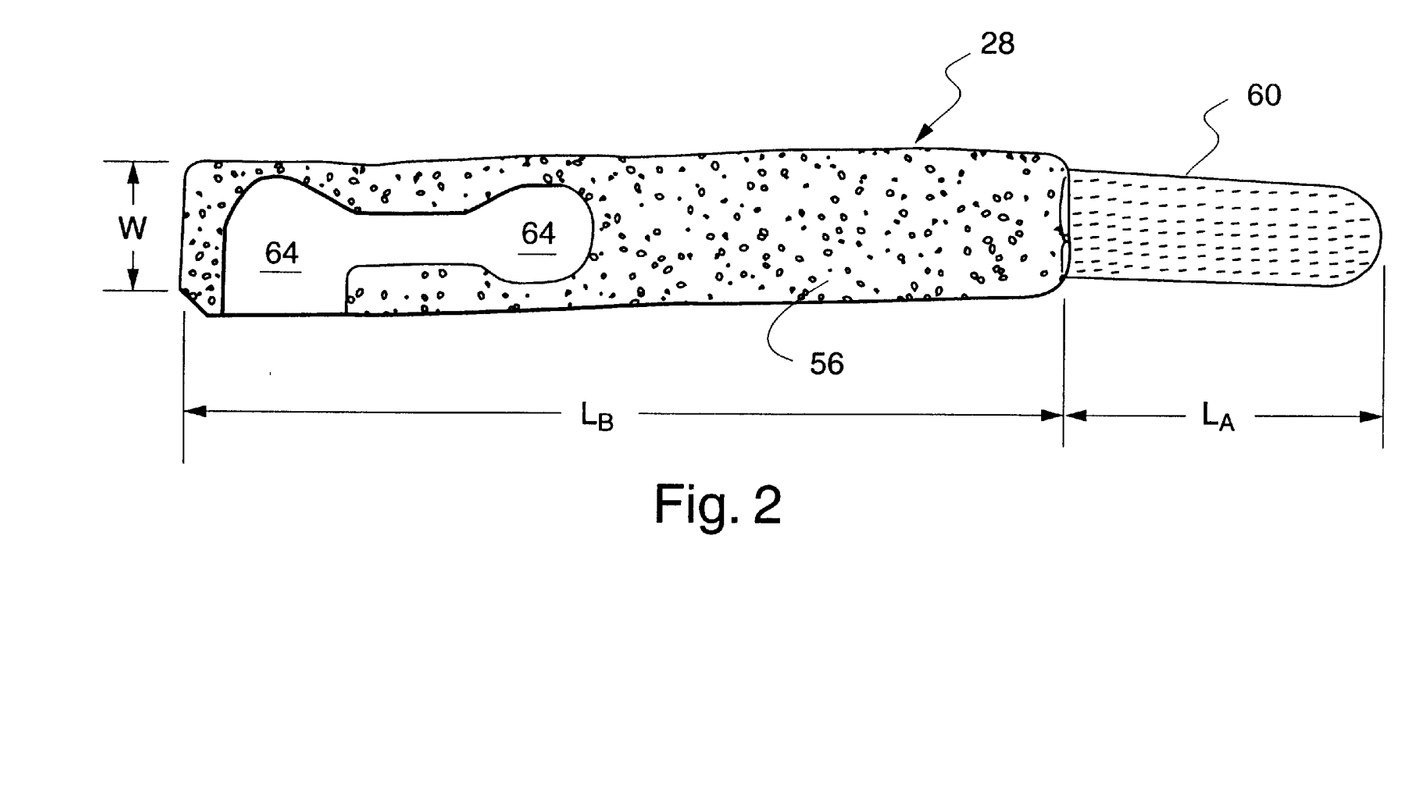
Figure 3:
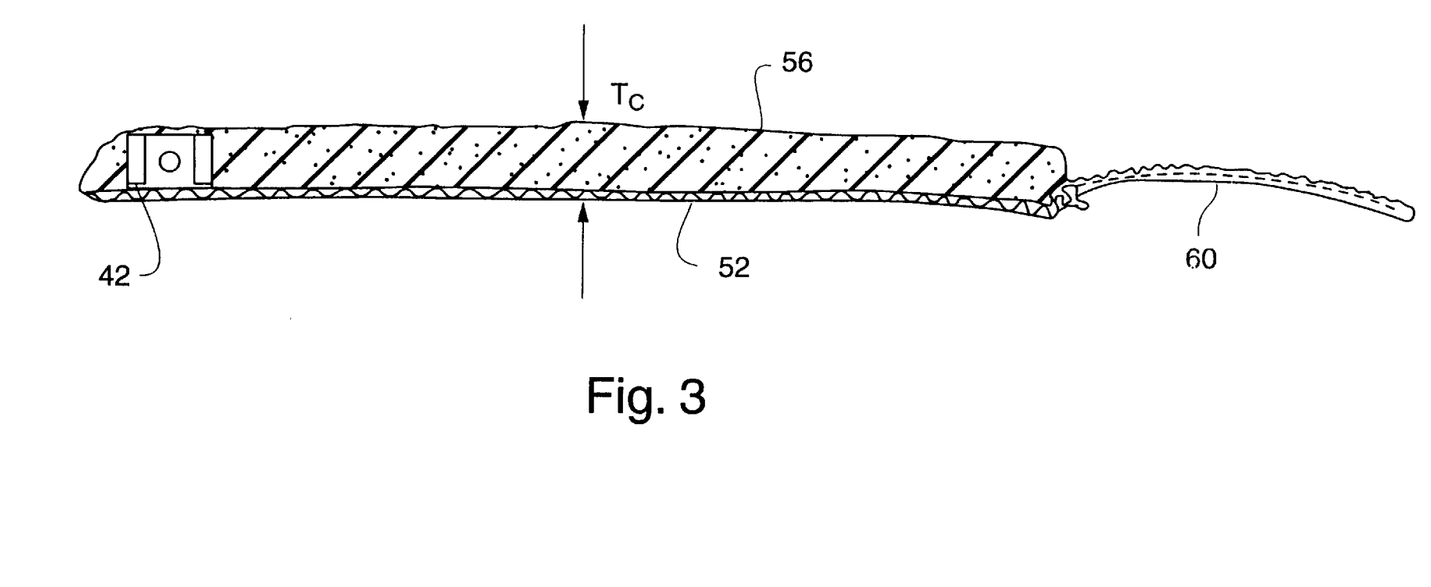
FIG. 3 is a side view of the sensor and carrier.
Figure 4:
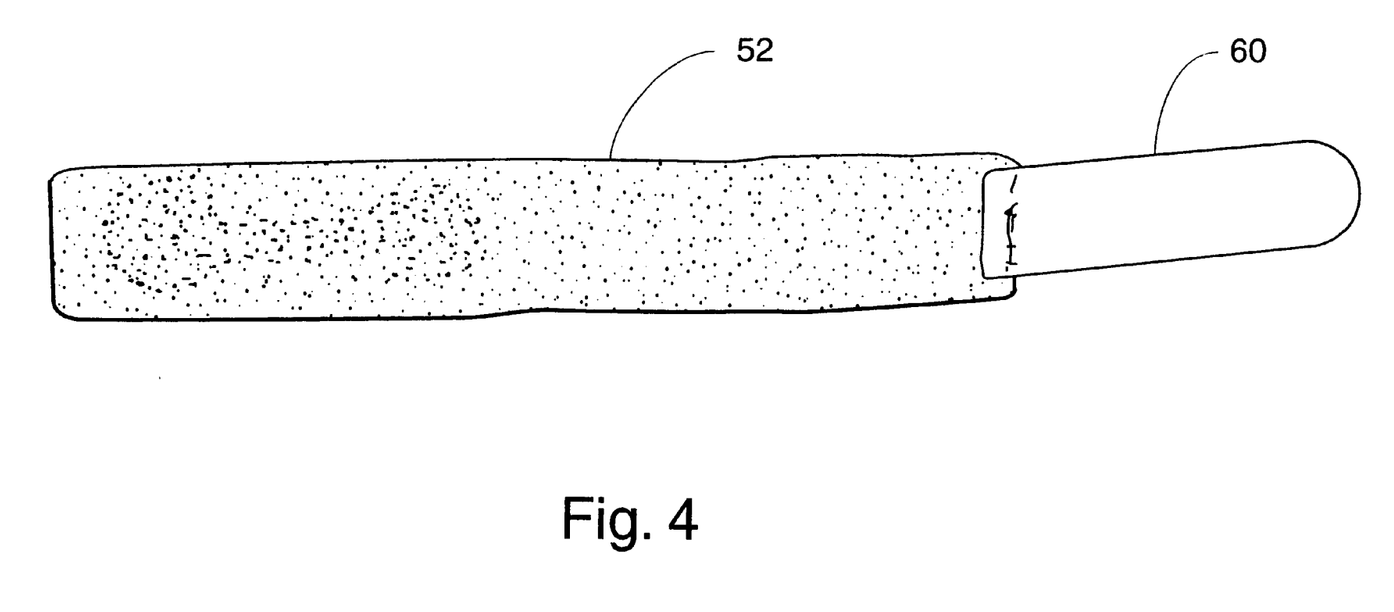
FIG. 4 is a bottom view of the carrier showing the backing material.
Figure 5:
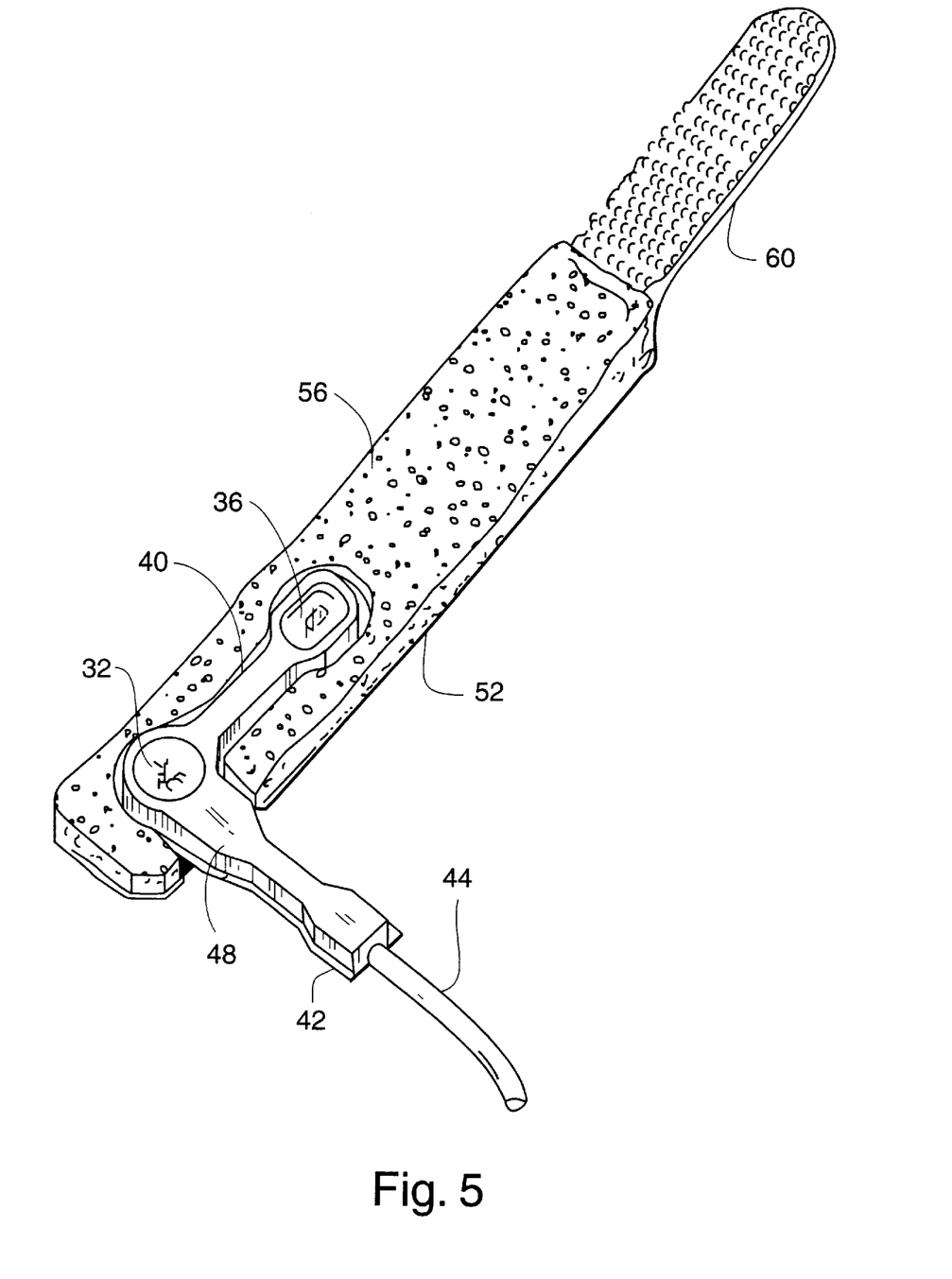
FIG. 5 is a perspective view of the sensor and carrier.
Figure 6:
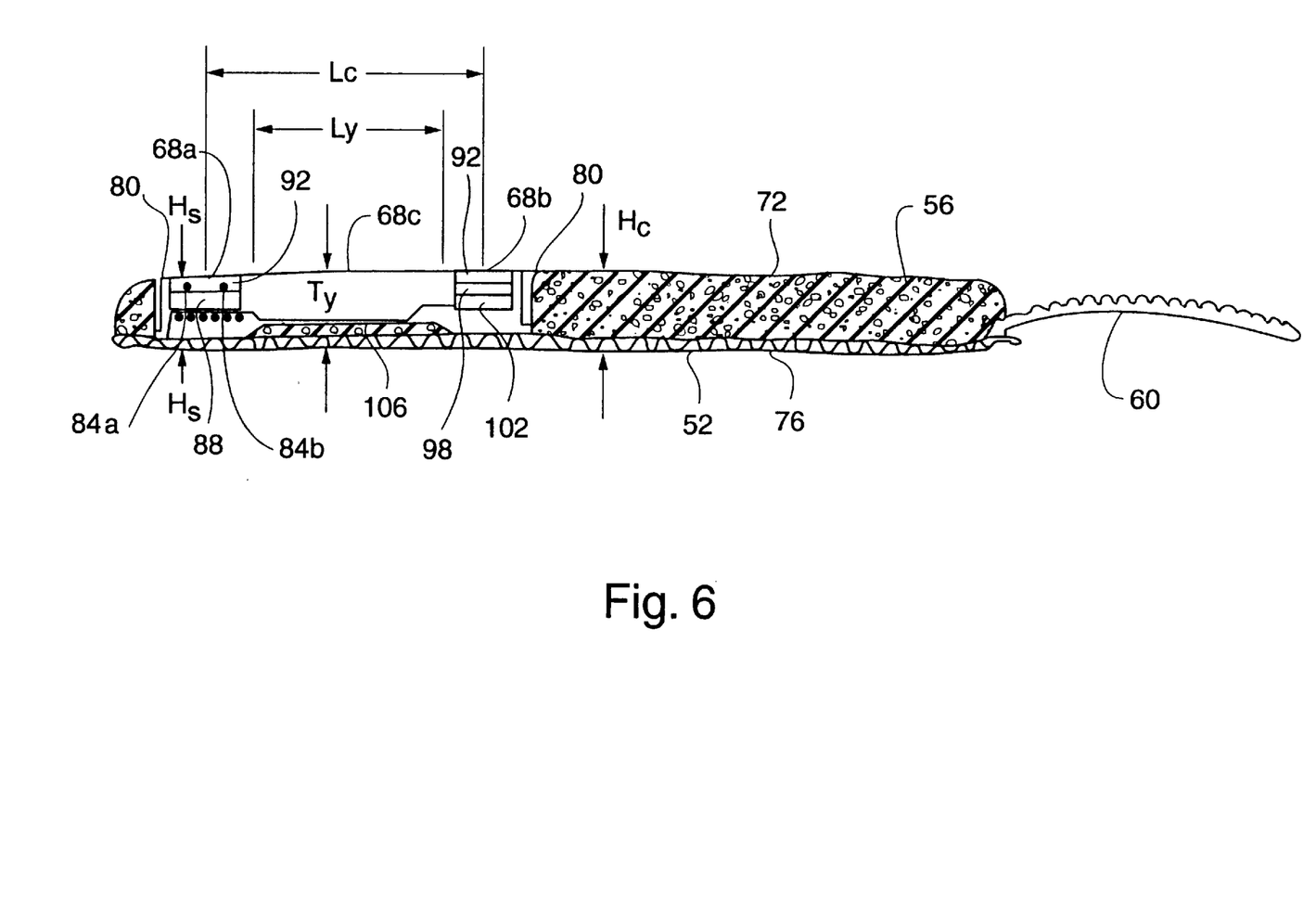
FIG. 6 is a cross-sectional view of the sensor and carrier taken along line A—A in FIG. 1.

The emitter assembly 32 in the sensor 24 includes two emitters 84a,b having complementary spectral contents deposited on a substrate 88 and covered by a light transparent lens 92a to form a substantially level face of the sensor 24 for contacting the patient's skin. The emitter assembly 32 can be a single broad-band emitter broken into individual bands of red and infrared light by separate interference filters or, as shown in FIG. 6, separate emitters, such as LEDs. The emitters 84a,b emit radiation 96 in the direction shown in FIG. 8.

Returning to FIGS. 1–6, the detector 36 in the sensor preferably has a large dynamic range to receive the portion of the radiation 96 that is not absorbed by the bloodstream surrounding tissue. The preferred detector is a silicone photodiode 98 deposited on a substrate 102 and covered by a light transparent lens 92b. The silicone photodiode 98 has an output linearly proportional to the incident light level over a range of 10 decades of light intensity, has low noise levels, is lightweight and small, and responds to light through the visible region up to a wavelength of about 1,100 nm.

It is preferred that the front surfaces 68 a,b,c of the yoke 40 and lenses covering the emitter assembly, and detector physically contact the surface of the patient's skin.

The housing encapsulating the emitter assembly 32 and detector includes the yoke 40 which carries conductive leads 106 for transmitting measurement information collected by the detector to the oximeter and a lip 42 extending around the perimeter of the base of the housing to secure the housing to the carrier 28 and to seal the upper and lower portions of the housing. The length "$L_Y$" of the yoke depends upon the body part to which the sensing device 20 is to be attached. In most applications, the sensor will be attached to a patient's foot, ankle, hand or wrist. To place the detector 36 and emitter assembly 32 in an opposing relationship as shown, the length of the yoke preferably ranges from about 1 to about 2 cm. This provides a distance "$L_C$" between the centers of the detector and the emitter assembly ranging from about 1.5 to about 4.0 cm and most preferably from about 2.5 to about 3.0 cm. The thickness "$T_Y$" of the yoke is less than the thicknesses of the opposing ends of the sensor as shown in FIG. 6, to facilitate flexure of the sensor when applied to the infant. Preferably the thickness "$T_Y$" ranges from about 0.05 to about 0.25 cm, more preferably from about 0.10 to about 0.20 cm, and most preferably from about 0.125 to about 0.175 cm. The housing is typically formed from an elastomeric material.

The compressible material 56 in the flexible carrier 28 physically contacts the patient's skin thereby cushioning the contact between the sensing device 20 and the skin. The compressible material has a compression setting that, upon application of a predetermined pressure to the material, substantially conforms to the surface contacting the compressible material. The material preferably is characterized by an indentation force of no more than about 100 lbs/50 in$^2$, more preferably no more than about 90 lbs/50 in$^2$, and most preferably ranging from about 12 to about 75 lbs/50in$^2$. According to the industry standard ASTM D-3574-86, the indentation force is the force required to produce a 25% deflection of the compressible material. The compressible material 56 preferably has a plurality of void spaces to permit compression. More preferably, the volume occupied by the compressible material 56 is at least about 50% by volume void space and most preferably the amount of void space ranges from about 60 to about 80% by volume. Preferred compressible material is open or closed cell foam, neoprene, rubber, fabric, and composites thereof, with foam being most preferred. To provide the necessary degree of compressibility, the compressible material preferably has a thickness "$T_C$" of at least about 0.4 cm and more preferably ranging from about 0.4 to about 1.5 cm. These features provide a compressible material having a density ranging from about 1.0 lbs/ft$^3$ to about 3 lbs/ft$^3$ with about 1.5 lbs/ft$^3$ being most preferred; an ultimate tensile strength ranging from about 15 to about 50 psi, with about 30 psi being most preferred; an ultimate elongation at break ranging from about 250 to about 500% with about 300 to about 450% being most preferred; and a tear resistance ranging from about 2 to about 10 ppi with about 3 to about 5 ppi being most preferred.

The backing material 52 in the flexible carrier 28 is adhesively bonded to the compressible material and sensor and imparts tensile strength to the carrier. A suitable backing material is highly flexible and has a relatively high tensile strength. The preferred backing material is cloth, foam, and composites thereof. The most preferred carrier 28 is formed from a composite material manufactured by a company having the tradename "POSEY COMPANY". This composite material has a soft cloth backing material attached to a soft, highly compressible foam.

The attachment strap 60 in the flexible carrier 28 includes a plurality of hooks that engage a plurality of loops on the front surface 76 of the backing material 52. The attachment strap is preferably a material sold under the trademark "VELCRO". As will be appreciated, the relative locations of the hooks and loops is not critical provided that the hooks and loops do not contact the skin and a suitable range of size adjustability is provided. Thus, the plurality of hooks can be located on the backing material 52 and the loops on the attachment strap 60. As will also be appreciated, the attachment strap 60 can fasten to the backing material in a number of other ways, such as by an adhesive coating on the strap or front surface 76 of the backing material.

The sensing device 20 is relatively small and lightweight for use with infants. The length "$L_S$" of the backing material 52 preferably ranges from about 7.5 to about 12.5 cm. The length "$L_A$" of the attachment strap 60 preferably ranges from about 2.5 to about 6.0 cm. The width "W" of the carrier 28 preferably ranges from about 1.25 to about 3.00 cm. The weight of the sensing device 20 is preferably about 1.5 g or less and most preferably ranges from about 0.5 to about 1.0 g.

Figure 7:
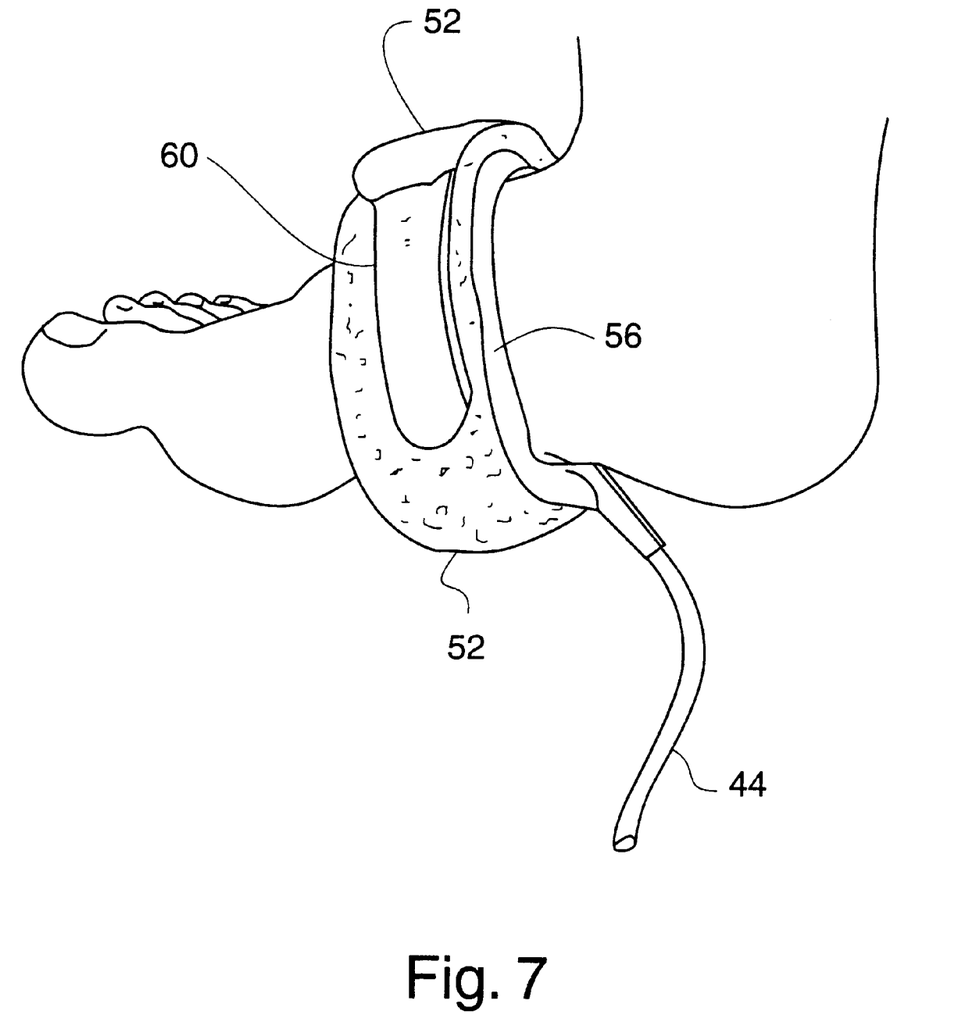
FIG. 7 is a perspective view of the sensor and carrier contacting the foot of a premature infant.
Figure 8:
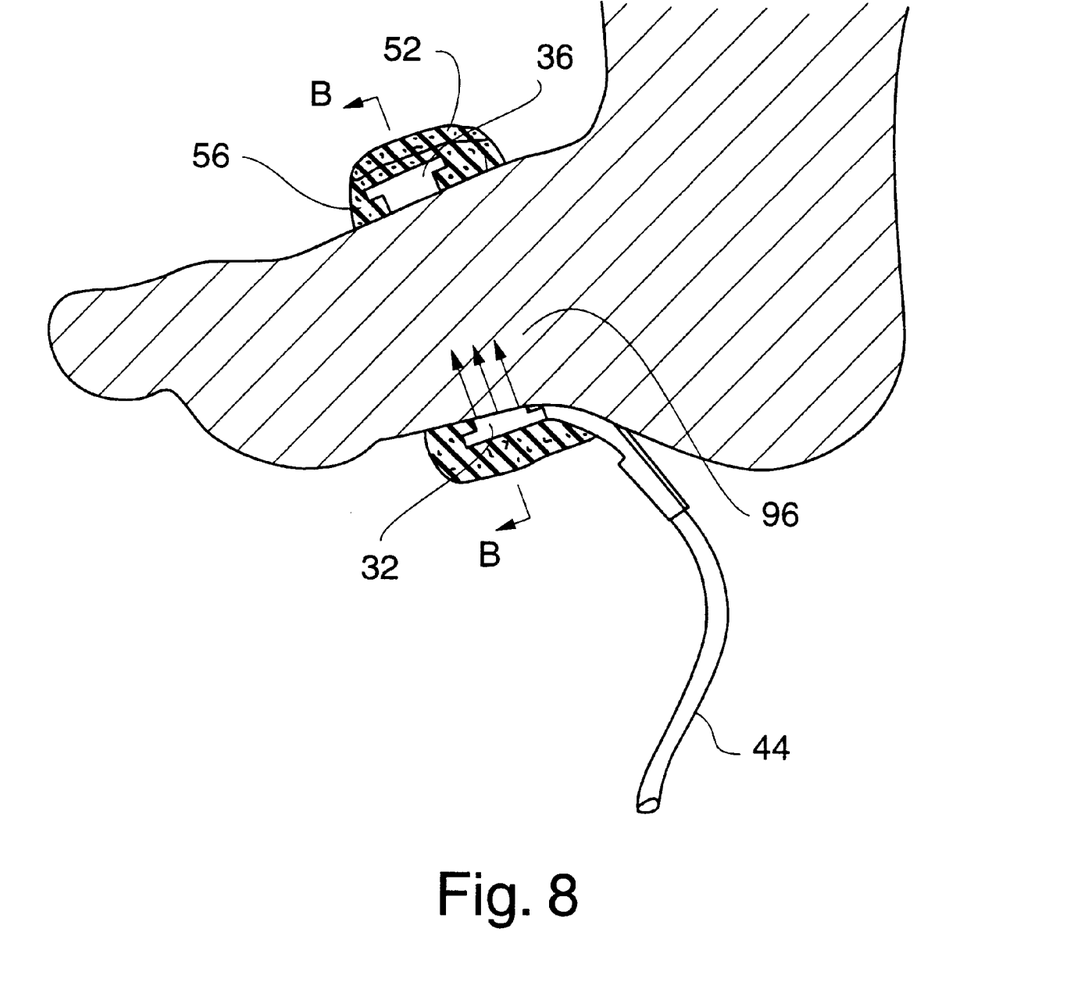
FIG. 8 is a cross-sectional view taken along the length of the foot in FIG. 7.
Figure 9:
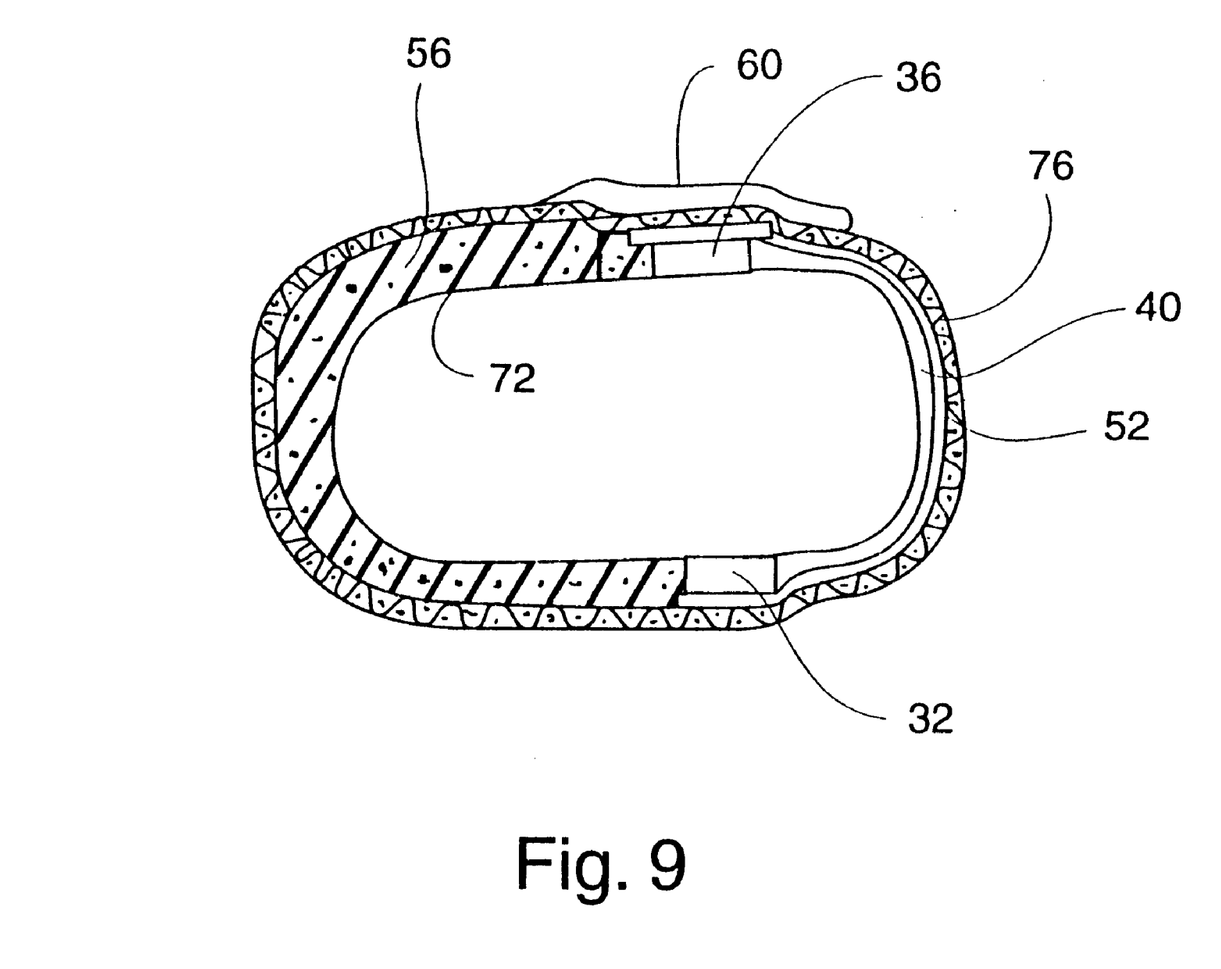
FIG. 9 is a cross-sectional view taken along line B—B in FIG. 8.

Referring to FIGS. 7–9, the method for using the sensor 20 will be discussed. Although the sensing device 20 is discussed with reference to an infant, the sensor can also be used in a variety of other applications where skin sensitivity is a concern, such as to measure the blood oxygen content of burn victims.

The flexible carrier 28 is attached to a body part of the infant, such as a foot, such that the detector 36 and emitter assembly 32 are in a substantially opposing relationship. To attach the carrier 28, the attachment strap 60 is attached to the front surface 76 of the backing material 52 as shown in FIG. 7. When attaching the carrier 28 to the body part, it is important not to pull the carrier 28 too tightly around the body part to avoid impairment of blood flow. Preferably, the pressure exerted on the body part by the measuring means and compressible material is no more than about 3 psi and most preferably no more than about 1 psi. Under these pressures, the thickness of the compressible material will decrease (i.e., compress) by an amount ranging from about 20 to 40% of the original (uncompressed) thickness. As shown in the FIGS. 8–9, when the carrier 28 is attached to the body part, the front surface 72 of the compressible material is substantially level with the front surfaces 68a,b of the detector and emitters. Thus, the front surfaces 68a,b of the lenses covering detector and radiation source are generally substantially level relative to one another.

Radiation 96 is passed from the emitters 84a,b through the infant's bloodstream and surrounding tissue with a portion of radiation being absorbed by the bloodstream and surrounding tissue (i.e., absorbed radiation portion) and another portion being passed by the bloodstream and surrounding tissue (i.e., unabsorbed radiation portion).

The unabsorbed radiation portion is received by the detector 36. A signal is generated by the detector in response to the contact of the unabsorbed radiation portion with the detector.

The signal is transmitted through the conductive leads 44 to an oximeter processing and display unit (not shown) that processes the signal and determines the oxygen content of the bloodstream.

Figure 10:
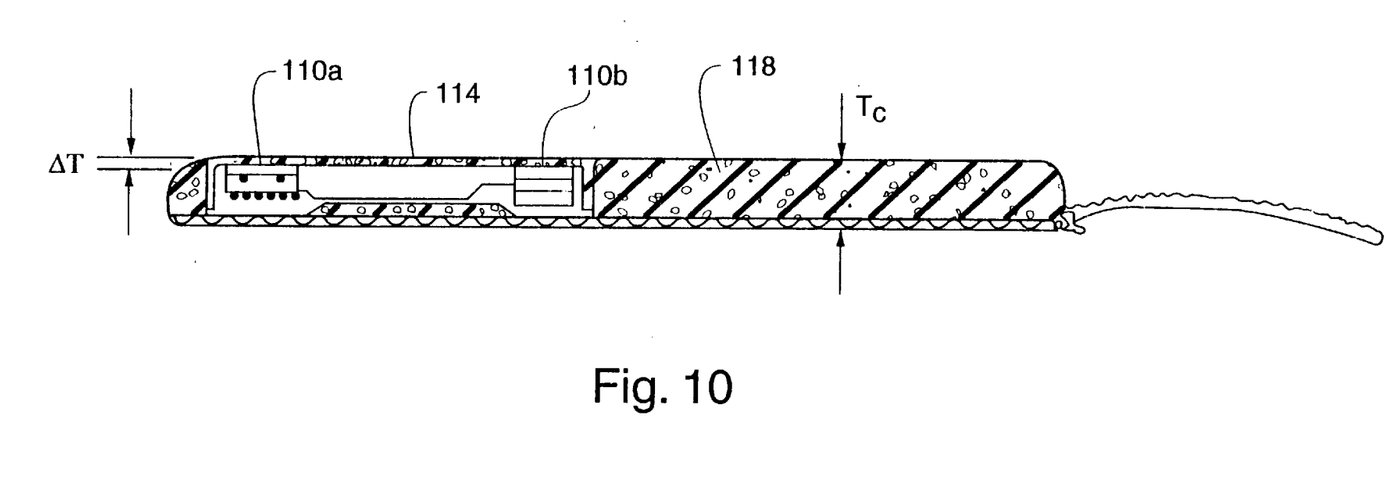
FIG. 10 is a cross-sectional view taken along line A—A of another embodiment of the sensor and carrier of the present invention.

An alternative embodiment of the sensing device of the present invention is depicted in FIG. 10. The alternative embodiment is substantially the same as the embodiment discussed above except that the front surfaces of the lenses covering the detector and emitter assembly 110a,b are offset by a distance "$\Delta T$" from the front surface 114 of the compressible material 118. The distance "$\Delta T$" is selected such that, when the compressible material is compressed by attachment to the body part of an infant, the thickness "$T_C$" of the compressed material above the backing material is no less than the maximum thickness of the sensor above the backing material. It is preferred that the front surfaces 110a,b be substantially coplanar with the front surface 114 of the compressed compressible material. The distance "$\Delta T$" is preferably no less than about 40% and more preferably no less than about 30% of the thickness "$T_C$" of the compressible material. In most applications, the distance $\Delta T$ ranges from about 0.3 to about 0.6 cm and most preferably from about 0.4 to about 0.5 cm. In this embodiment, the thickness of the sensor is no more than the height of the cavity walls when the compressible material is compressed to the desired degree.

Figure 11:
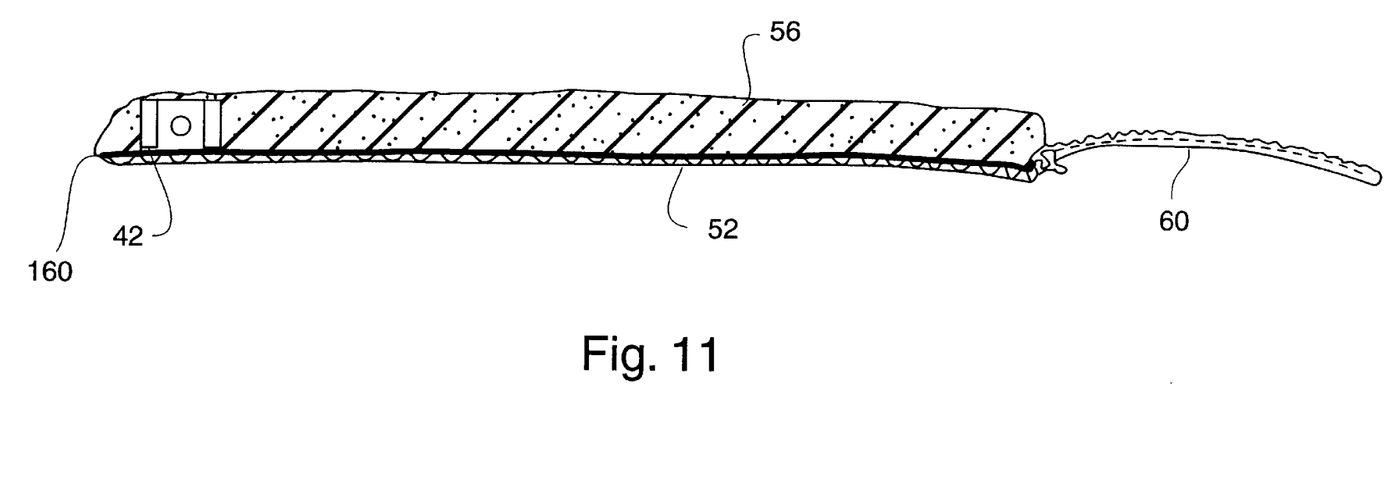
FIGS. 11 and 12 are side and top views of yet another embodiment of the sensor and carrier.
Figure 12:
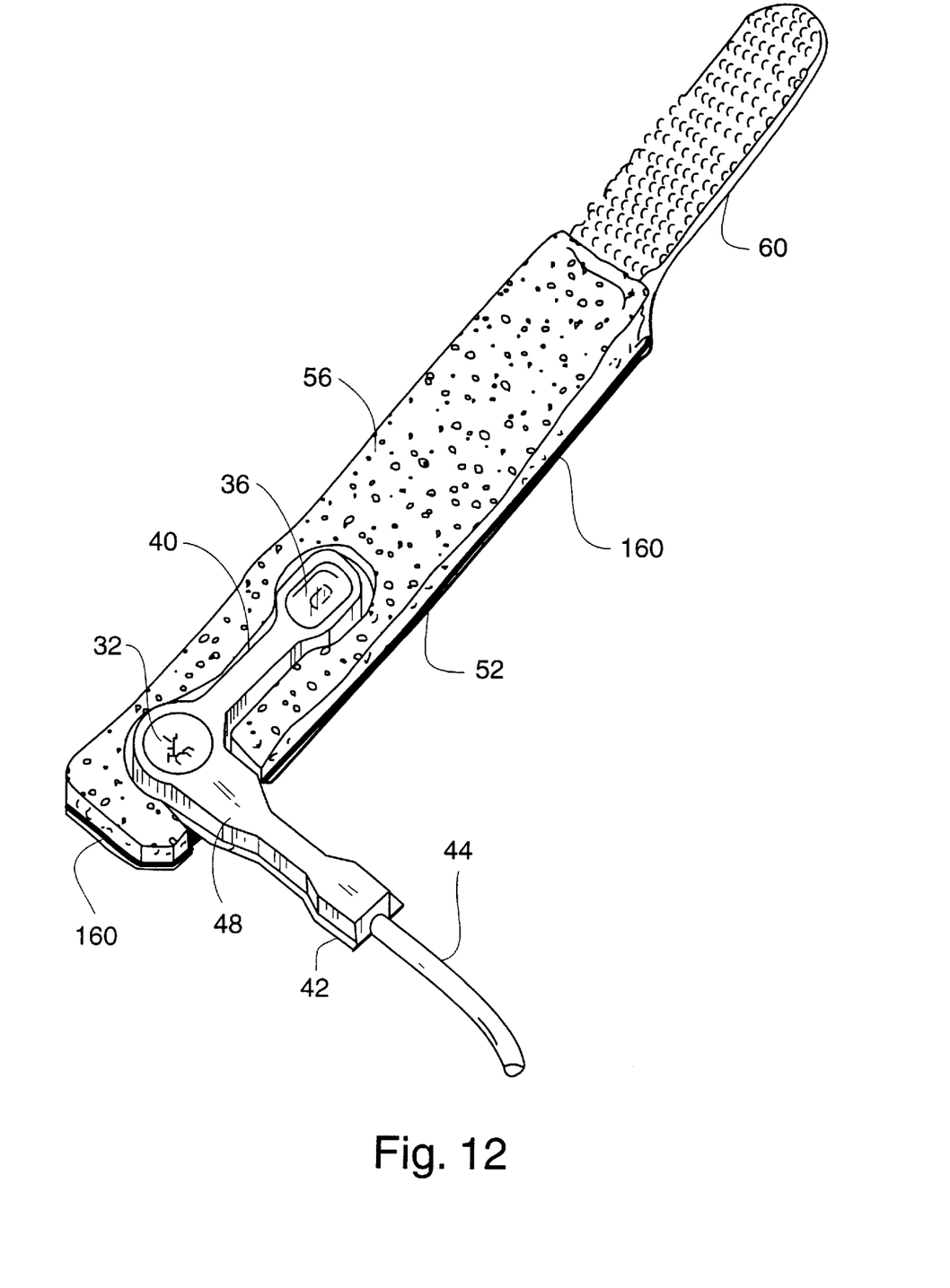

Another embodiment of the sensing device of the present invention is depicted in FIGS. 11 and 12. The embodiment is substantially the same as the embodiment shown in FIGS. 1–9, except that an additional light impermeable layer 160 is included to reduce noise effects of ambient light. The light impermeable layer 160 is located between the compressible material and backing material and extends the length "$L_B$" and width "W" of the sensor. The layer 160 can be formed from a variety of materials, including fabric, foam and composites thereof. The layer 160 is substantially opaque to ambient light, preferably blocking from about 75 to about 100% and more preferably from about 90 to about 100% of the ambient light from passing through the layer 160.

In yet another alternative embodiment, the compressible material 56 can be substantially opaque to light. In this embodiment, it would be unnecessary to have a separate light impermeable layer 160 as shown in FIG. 11.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A device for measuring the oxygen content of a patient's bloodstream, comprising:
   (a) measuring means for measuring the oxygen content of a patient's blood, said measuring means having a front surface adapted for contacting a patient's tissue; and
   (b) flexible carrier means for engaging the measuring means with the patient's tissue, the flexible carrier means including a compressible material, a backing material, and a fastener adapted for contacting the front surface of the measuring means with the patient's tissue, the compressible material being adapted to be located between the backing material and the patient's tissue, the measuring means being at least partially nested in a recess in the compressible material, the measuring means being engageable with the patient's tissue so that the compressible material substantially conforms to the patient's tissue and the measuring means and compressible material adjacent to the measuring means apply a substantially even pressure to the patient's tissue.

2. The device of claim 1, wherein the measuring means comprises an emitter spaced a distance from a detector, the distance between the emitter and detector ranging from about 1.5 to about 4.0 cm.

3. The device of claim 1, wherein the compressible material is selected from the group consisting of foam, neoprene, rubber, fabric, and composites thereof.

4. The device of claim 1, wherein the compressible material has a thickness ranging from about 0.4 to about 1.5 cm.

5. The device of claim 4, wherein the compressible material has an indentation force of no more than 100 lbs/50 in$^2$.

6. The device of claim 1, the compressible material being adapted to physically contact the patient's tissue.

7. The device of claim 1, wherein the backing material is selected from the group consisting of cloth, foam, and composites thereof.

8. The device of claim 1, wherein the flexible carrier means includes a plurality of hooks and a plurality of matching loops for engaging the measuring means with the patient's tissue.

9. The device of claim 1, the measuring means and flexible carrier means being adapted to apply pressure substantially uniformly to the patient's tissue substantially throughout the area of contact between the front surfaces of the measuring means and flexible carrier means on the one hand and the patient's tissue on the other.

10. The device of claim 1, wherein a first portion of the flexible carrier means is engageable with a second portion of the flexible carrier means to engage the measuring means with the patient's tissue.

11. The device of claim 1, wherein the measuring means and compressible material adjacent thereto have substantially the same thickness.

12. The device of claim 1, wherein the flexible carrier means is adapted to substantially non-adhesively contact the patient's tissue.

13. The device of claim 1, wherein at least one of the recess and measuring means comprises a substantially light opaque adhesive to attach the measuring means in the recess.

14. A device for measuring the oxygen content of a patient's bloodstream, comprising:
   (a) a sensor for measuring the oxygen content of a patient's blood, said sensor having a front surface adapted for contacting a patient's tissue; and
   (b) a flexible carrier adapted for engaging the sensor with the patient's tissue, the flexible carrier including a compressible material having front and rear surfaces, with the front surface being adapted to be located adjacent to the patient's tissue, a recess sized for receiving at least a portion of said sensor, and a backing material located adjacent said rear surface of the compressible material, the sensor and flexible carrier being engageable with the patient's tissue so that the front surface of the compressible material adjacent to the sensor and the front surface of the sensor apply a substantially uniform pressure to the patient's tissue.

15. The device of claim 14, wherein the compressible material adjacent to the sensor has a thickness that is at least the thickness of the sensor.

16. The device of claim 14, wherein, before the sensor is engaged with the patient's tissue, the compressible material has a first thickness and the sensor has a second thickness and the first thickness is more than the second thickness.

17. The device of claim 16, wherein the second thickness is about 90% or less of the first thickness.

18. The device of claim 14, wherein the front surface of the compressible material and the front surface of the sensor are substantially free of adhesive so that the sensor and the flexible carrier are engageable with the patient's tissue with substantially no adhesive bonding of the sensor and the flexible carrier to the patient's tissue.

19. The device of claim 14, wherein the compressible material substantially surrounds the perimeter of the sensor.

20. The device of claim 14, wherein the compressible material is at least one of a foam, neoprene, rubber, fabric, and composites thereof and said compressible material has a thickness ranging from about 0.4 to about 1.5 cm.

21. The device of claim 14, wherein the compressible material has an indentation force of no more than about 100 lbs/50 in$^2$.

22. The device of claim 14, wherein the flexible carrier includes a substantially light opaque layer.

23. The device of claim 14, wherein the sensor is substantially entirely disposed within said recess.

24. The device of claim 23, wherein the front surface of the sensor and the front surface of the compressible material adjacent thereto are substantially level.

25. The device of claim 23, Wherein the front surface of the sensor is recessed, within said recess, a distance relative to the front surface of the compressible material, in an uncompressed state, adjacent to the sensor.

26. The device of claim 25, wherein the compressible material has an uncompressed thickness of at least about 0.4 cm and said distance is at least about 30% of the thickness of the compressible material adjacent to the sensor.

27. The device of claim 26, wherein said distance is at least about 0.3 cm.

28. The device of claim 25, wherein the compressible material is compressible so that, when the compressible material adjacent to the sensor is in a compressed state with the front surface of the compressible material substantially level with the front surface of the sensor, the front surface of the compressible material, adjacent to the sensor, exerts a pressure of no more than about 3 psi.

29. The device of claim 28, wherein said pressure is no more than about 1 psi.

30. The device of claim 28, wherein the thickness of the compressible material in said compressed state is at least about 20% smaller than the thickness of the compressible material in said uncompressed state, the thickness of the compressible material in the uncompressed state being at least about 0.4 cm.

31. The device of claim 14, wherein the compressible material has a side surface forming a wall of at least a portion of the recess.

32. The device of claim 31, wherein said wall extends substantially entirely across the entire thickness of the compressible material.

33. A method for measuring the oxygen content of a patient's bloodstream, comprising the steps of:

contacting a carrier, including a compressible material mounted on a backing material, and a sensor for measuring the oxygen saturation with the patient's tissue;

engaging a portion of the carrier with another portion of the carrier to attach the carrier to the patient with substantially uniform pressure being applied to the patient by the sensor and the compressible material adjacent to the sensor;

passing radiation from an emitter in the sensor through the bloodstream such that a portion of the radiation is absorbed by the bloodstream and a portion of the radiation is passed by the bloodstream;

receiving at least a portion of the passed radiation portion with a detector in the sensor; and determining the oxygen content of the bloodstream based on the received passed radiation portion.

34. The method of claim 33, wherein said carrier, where in contact with said patient's tissue, being substantially free of an adhesive bond to said patient's tissue.

35. The method of claim 33, wherein said contacting step comprises:

wrapping said compressible material and said sensor around a body part of the patient; and the engaging step comprises:

aligning said emitter and detector such that radiation generated by said emitter can be received by said detector; and engaging a plurality of hooks with a plurality of loops to hold the compressible material and sensor in position on said body part.

36. The method of claim 33, wherein said engaging step comprises:

releasably connecting a first end of the carrier with a second end of the carrier.

37. The method of claim 33, wherein the sensor, prior to the contacting step, is at least partially disposed in a recess in said compressible material.

38. The method of claim 37, wherein the compressible material includes a first front surface, adjacent to the sensor, that contact:, the patient following the engaging step, and the sensor includes a second front surface that contacts the patient following the engaging step; and prior to said engaging step, said second front surface is recessed, in said recess, relative to said first front surface, and after said engaging step, said second front surface is substantially coplanar with said first front surface.

39. The method of claim 38, wherein the compressible material, adjacent to said sensor, has a first thickness prior to the engaging step; and the engaging step comprises compressing the compressible material, adjacent to the sensor, to a second thickness that is smaller than said first thickness.

* * * * *

UNITED STATES PATENT AND TRADEMARK OFFICE
CERTIFICATE OF CORRECTION

PATENT NO. : 5,919,133
DATED : July 6, 1999
INVENTOR(S) : TAYLOR et al.

It is certified that error appears in the above-identified patent and that said Letters Patent is hereby corrected as shown below:

At Column 8, line 45, delete the word "the" and insert --a-- therefor.
At Column 10, line 47, delete the word "contact:" and insert --contacts-- therefor.

Signed and Sealed this

Seventh Day of December, 1999

Attest:

Q. TODD DICKINSON

*Attesting Officer*   Acting Commissioner of Patents and Trademarks